United States Patent [19]

Dumas et al.

[11] Patent Number: 5,801,192
[45] Date of Patent: Sep. 1, 1998

[54] USE OF VITAMIN C OR DERIVATIVES OR ANALOGUES THEREOF PROMOTING SKIN ELASTIN SYNTHESIS

[75] Inventors: Marc Dumas, Colombes; Frédéric Bonte; Alain Meybeck, both of Courbevoie; Catherine Chaudagne, Chatou, all of France

[73] Assignee: LVMH Recherche, Nanterre, France

[21] Appl. No.: 817,978

[22] PCT Filed: May 10, 1996

[86] PCT No.: PCT/IB96/00444

§ 371 Date: Apr. 25, 1997

§ 102(e) Date: Apr. 25, 1997

[87] PCT Pub. No.: WO96/19099

PCT Pub. Date: Jun. 27, 1996

[30] Foreign Application Priority Data

Aug. 25, 1995 [FR] France ................... 95 10093

[51] Int. Cl.[6] ................... A61K 31/34
[52] U.S. Cl. ................... 514/474
[58] Field of Search ................... 514/474

[56] References Cited

U.S. PATENT DOCUMENTS

| | | | |
|---|---|---|---|
| 4,938,969 | 7/1990 | Schinitsky et al. | 424/642 |
| 4,983,382 | 1/1991 | Wilmott et al. | 424/62 |

FOREIGN PATENT DOCUMENTS

| | | |
|---|---|---|
| 282746 | 9/1988 | European Pat. Off. . |
| 2612775 | 9/1988 | France . |
| 2666226 | 3/1992 | France . |
| 2735982 | 3/1997 | France . |
| 4419783 | 12/1995 | Germany . |
| 95/25524 | 9/1995 | WIPO . |

OTHER PUBLICATIONS

Biosis AN95:257264, Bonte et al, 1995.
WPIDS AN 93-357127, Oct. 12, 1993.
Medline AN, Barnes, 1969.
University Medical Products, Facelift™, 1995.
Dumas et al., "In Vitro Biosynthesis of Type I and III Collagens by Human Dermal Fibroblasts from Donors of Increasing Age", *Mechansims of Ageing and Development*, vol. 73 (1994) pp. 179–187.
*Dorvault*, 23rd Edition, p. 1893, Edition Vigot, Jan. 1995.
Reference 855 Ascorbic Acid, Merck Index 1989, 11th Edition.
Phillips et al., "Effects of Ascorbic Acid on Proliferation and Collagen Synthesis in Relation to the Donor Age of Human Dermal Fibroblasts", *Journal of Investigative Dermatology*, vol. 103, No. 2, Aug. 1994, pp. 228–232.
Sephel et al., "Elastin Production in Human Skin Fibroblasts Cultures and Its Decline with Age", *Journal of Investigative Dermatology*, vol. 86, No. 3, Mar. 1986, pp. 279–285.
Takema et al., "Age-Related Changes in the Elastic Properties and Thickness of Human Facial Skin", *British Journal of Dermatology*, vol. 131, 1994, pp. 641–648.
*Patent Abstracts of Japan*, vol. 12, No. 306 (C–522) [3153], JP.A.63 079809 (Shisiedo) 1986.
*Chemical Abstracts*, vol. 72, nA 29295 1969.
*Chemical Abstracts*, vol. 118, nA 66557 1993.

*Primary Examiner*—Rebecca Cook
*Attorney, Agent, or Firm*—Beveridge, DeGrandi, Weilacher & Young LLP

[57] ABSTRACT

The invention relates to the use of ascorbic acid, notably L-ascorbic acid or vitamin C, or of its erythorbic acid isomer, or of their salts or esters, for promoting the synthesis of elastin in the dermis in the view of improving in particular skin elasticity.

The invention enables manufacturing cosmetic or pharmaceutical compositions, notably dermatological compositions, for improving skin elasticity, for example in the context of a product which improves skin tone or skin firmness.

The invention also enables increasing the elastin content of artificial dermes.

24 Claims, No Drawings

USE OF VITAMIN C OR DERIVATIVES OR ANALOGUES THEREOF PROMOTING SKIN ELASTIN SYNTHESIS

This is a 371 of PCT/IB96/00444 filed May 10, 1996.

The present invention relates essentially to the use of ascorbic acid, notably L-ascorbic acid or vitamin C, or of its isoascorbic acid isomer, called erythorbic acid, or salts or esters thereof, for promoting skin elastin synthesis. In the following part of the present description, the whole of these compounds is referred to under the generic name of <<ascorbic derivative >>for simplicity.

Vitamin C, or ascorbic acid, has been known for a long time for physiological activities such as an antiscorbutic, or an antioxidant such as described by DORVAULT, 23rd Edition, page 1893, edition Vigot, January 1995, or in the Merck Index 1989, 11th Edition, reference 855.

Furthermore, it is known from the article of C. L. Phillips et al. in J. Invest. Dermatol. 1994, 103, pages 228–232, that ascorbic acid favours the synthesis of collagen by fibroblasts of the human dermis, collagen contributing essentially to the resistance qualities of the skin against constraints which are applied thereto.

Furthermore, it is known from the article by Gregory C. Sephel et al. in J. Invest. Dermatol. 1986, 86, pages 279–285, that the production of elastin by the fibroblasts of aged donors diminishes. It is also known that the skin elasticity decreases significantly with age, as described by Takema et al. in British Journal of Dermatology 1994, 131 pages 641–648.

Within the context of the invention, it has been demonstrated in an unexpected way that these ascorbic derivatives enabled promoting the synthesis of elastin by the fibroblasts of the dermis, particularly the fibroblasts of the human dermis.

It shall be borne in mind now that in the dermis, the elastic fibres form a network which contributes to the elasticity of the skin and accordingly to its tone and firmness. Elastin is the major component of these fibres, and is initially synthesised by the fibroblasts in the form of a soluble polypeptide of 70 kDa which is tropoelastin. The formation of the microfibrils then takes place via intramolecular bonds, called desmosines, between the lysine residues of the polypeptide chains. These bonds confer a great insolubility to elastin.

Thus, an aim of the present invention is to solve the novel technical problem consisting of providing a solution which enables improving the skin elasticity in favouring the synthesis of elastin, according to one simply conceived solution which is easily usable on an industrial scale whilst still enabling a cosmetic or pharmaceutical, notably dermatological use.

Thus, according to a first aspect, the present invention relates to the use of ascorbic acid, particularly L-ascorbic acid or vitamin C, or of its erythorbic acid isomer, or salts or esters thereof, referred to under the generic name of ascorbic derivative, as cosmetic agent intended for promoting the synthesis of elastin by the fibroblasts of the dermis, with a view to improve particularly the skin elasticity, skin tone or to favour skin firmness.

According to a second aspect, the invention also relates to the use of ascorbic acid, in particular L-ascorbic acid or vitamin C, or of its erythorbic acid isomer, or salts or esters thereof, referred to under the generic name of ascorbic derivative, for the preparation of a pharmaceutical composition, notably dermatological composition, intended for promoting the synthesis of elastin by the fibroblasts of the dermis, with the view to improve particularly the skin elasticity, skin tone or to favour skin firmness.

Of course, the above-mentioned ascorbic derivative may be used both in a curative and in a preventative manner for correcting or preventing the loss of elasticity, tone or firmness of the skin, which is due notably to ageing or to the exposure to UV rays.

According to an advantageous embodiment, the above-mentioned ascorbic derivative is used topically at a concentration between 0.001% and 5% with respect to the total weight of a composition containing same in an appropriate excipient, vehicle or support, preferably cosmetically or pharmaceutically, notably dermatologically acceptable. A preferred concentration is between 0.01 and 1% by weight with respect to the total weight of the composition containing same.

According to a particular variant, the above-mentioned ascorbic derivative is selected from the group consisting of ascorbic acid, sodium ascorbate, magnesium ascorbate, sodium ascorbyl phosphate, magnesium ascorbyl phosphate, erythorbic acid, sodium erythorbate, magnesium erythorbate, and acetic, propionic and palmitic esters of ascorbic and erythorbic acids.

According to an advantageous embodiment of the invention, the ascorbic derivative according to the invention is used in combination with an effective amount of an active principle which promotes the synthesis of the components of the extracellular matrix of the dermis, amongst which are collagen, in particular collagen I and collagen III, and glycosaminoglycans.

Madecassoside, a Centella asiatica extract, or a ginseng extract, in particular a ginsenoside $R_o$-containing extract, is used as an example of an active principle which promotes the synthesis of collagen, said active principle being at a concentration between 0.01% and 5% by weight with respect to the total weight of the final composition.

A vegetable extract such as a Filicium decipens extract, in particular an extract of the bark of the root of this plant, described in the French patent Publication No. 2,735,982, or a growth factor, in particular PDGF (platelet derived growth factor), a growth factor derived from blood platelets, will be used as example of an active principle which promotes the synthesis of glycosaminoglycans.

According to another advantageous embodiment, the above-mentioned ascorbic derivative is used in combination with a vitamin, in particular vitamin A, its palmitic, propionic or acetic ester, or vitamin E and its derivatives, particularly at a concentration between 0.0001 and 5% by weight with respect to the total weight of the composition.

According to a third aspect, the present invention also covers a method of cosmetic or therapeutic treatment of the skin which is intended for preventing or correcting a loss of skin elasticity, tone or firmness, characterised in that it comprises the application onto the zones of the skin to be treated of an effective amount of an ascorbic derivative selected from the group consisting of ascorbic acid, in particular L-ascorbic acid or vitamin C, erythorbic acid, and a cosmetically or pharmaceutically acceptable salt or ester thereof, for promoting the synthesis of elastin by fibroblasts, said ascorbic derivative being incorporated in a cosmetically or pharmaceutically acceptable excipient.

The variants of this method also clearly result from the variants of the above-mentioned use.

It results from the foregoing that the ascorbic derivatives according to the invention are precious for the manufacture of a cosmetic, pharmaceutical, notably dermatological composition, where an improvement of the skin elasticity is sought.

The person skilled in the art thus understands the major interest of the invention which favours the synthesis of elastin and its ease of use due to a topical application on the skin.

According to a fourth aspect, the present invention also covers a method of preparing an artificial skin obtained by fibroblast culture, characterised in that an effective amount of an ascorbic derivative, such as defined above, is used during at least one cell culture step in order to increase the elastin content of the artificial skin thus prepared.

According to an advantageous variant, the fibroblasts used for the preparation of the artificial skin are fibroblasts from the human dermis.

According to another advantageous variant, the ascorbic derivative is incorporated in the cell culture medium, preferably at a concentration between 5 micromoles per litre and 150 micromoles per litre of medium, or, advantageously, between 10 micromoles per litre and 50 micromoles per litre of medium.

A culture medium which is commercially available and generally used for fibroblast culture may for example be used, such as the MEM medium, to which an effective concentration of ascorbic derivative will be added, in particular for example sodium ascorbate, particularly at a concentration between the values indicated above.

Other aims, characteristics and advantages of the invention shall appear clearly in the light of the following explanatory description made with reference to the examples given hereinafter which are given as illustration and which in no way limit the scope of the invention.

In the examples, all the percentages are given by weight unless indicated otherwise.

EXAMPLE 1

Example of an experiment demonstrating the promotion of the synthesis of elastin by human skin fibroblasts Materials and method Origin of the cells:

A strain of normal human fibroblasts (NHF) originating from surgical skin from the face of a 50 year old woman. The cells were obtained by the explants method such as described by M. Dumas et al. in the article entitled "in vitro biosynthesis of type I and III collagens by human dermal fibroblasts from donors of increasing ages" in Mech. Ageing Dev. 73 (1994), pages 179–187.

Preparation of the solutions of the products to be tested:

These normal human skin fibroblasts thus obtained are sown in wells of a multi-well culture box, in an E 199 culture medium, in which 2 millimoles per litre of L-glutamine were added.

24 Hours after sowing, certain wells received sodium ascorbate at 25 or 150 micromoles per litre, or sodium ascorbyl phosphate at 25 or 150 micromoles per litre.

Six wells per product and per concentration are used each time, as well as six wells which receive no product to be tested for the control cultures.

The culture is pursued for 48 hours.

After 48 hours of culture as indicated above, the elastin secreted is determined on the supernatents by an ELISA method derived from that used in the determination of collagen as described by M. Dumas et aL in the above-mentioned publication, with the only difference that a commercial human anti-elastin polyclonal antibody was used instead of human anti-collagen I and III polyclonal antibody.

Naturally, this determination is carried out also on the control cultures which did not receive product to be tested.

A standard range carried out from commercial soluble elastin enables converting the optical density (OD) values obtained from the culture supernatants into nanogrammes of elastin.

Determination of the proteins:

In parallel with the determination of elastin, a determination of cell proteins is carried out on the fibroblast cultures, after the removal of the supernatant, in order to bring the amount of elastin determined to a fixed amount of cell proteins. The determination is effected using the BCA-1 kit (Bicinchoninic acid kit, marketed by Sigma, France) after dissolving the cell mass with 0.1 N sodium hydroxide solution.

Expression of the results and statistics:

The results are expressed in nanogrammes of elastin secreted per microgramme of cell proteins. The promoting activity A, expressed as a percentage, is calculated according to the following formula:

$$A = \frac{q - q_0}{q_0} \times 100$$

in which:

q represents the amount of elastin secreted by the treated NHFs, $q_0$ represents the amount of elastin secreted by the control NHFs.

The results obtained on the treated cultures (n=6) and control cultures (n=6) are compared with the aid of the Student t test for non-paired series. Any value of p<0.05 will indicate that a significant difference exists between the elastin secretion from the control NHFs and those treated with the products of the invention.

Table I gives the results of the test with sodium ascorbate while Table II gives the results with magnesium ascorbyl phosphate, designated as the abbreviation MgVCP, which is one of the cosmetically usable vitamin C derivatives.

TABLE I

| Experimental conditions | Elastin secreted ng/µg prot/48 h ± σ* | Activity A in % | Student t test p values |
|---|---|---|---|
| Control without Na ascorbate | 12.9 ± 1.6 | — | |
| Na ascorbate 25 µM | 23.9 ± 2.4 | 85 | <0.0001 |
| Na ascorbate 150 µM | 29.3 ± 4.2 | 127 | <0.0001 |

*σ: spread type or standard deviation

TABLE II

| Experimental conditions | Elastin secreted ng/µg prot/48 h ± σ | Activity A in % | Student t test p values |
|---|---|---|---|
| Control without MgVCP | 12.4 ± 1.6 | | |
| MgVCP 25 µM | 29.5 ± 3.8 | 137 | <0.0001 |
| MgVCP 150 µM | 33.7 ± 4.3 | 171 | <0.0001 |

Conclusions

As it arises from Tables I and II, sodium ascorbate, as for magnesium ascorbyl phosphate (MgVCP) strongly promote the synthesis of elastin. This promotion increases with the concentration of the product tested.

It is further observed that for the tests reported herein, the promoting activity of the synthesis of elastin is maximum (+171%) in the case of the cultures treated at 150µM of magnesium ascorbyl phosphate, which is remarkable, while this activity is at the minimum of 85% in the case of the cultures treated at 25 µM of sodium ascorbate, which is also exceptional. It is therefore demonstrated that the use of ascorbic acid or one of its derivatives, in particular a salt or an ester thereof, enables promoting the synthesis of elastin by the fibroblasts in a significant and particularly unexpected manner.

Examples of applications

The compositions are expressed below in percentages by weight.

EXAMPLE 2

Gel for face-care:
  magnesium ascorbyl phosphate ... 2
  hydrogenated lecithin ... 1
  Hyaluronic acid ... 1
  carbopol 941 ... 1.25
  water+preservative+triethanolamine ... qs for 100.

Applied locally twice a day onto the lower part of the face and the neck, this care product improves and maintains the firmness and the tone of the skin of the face and reduces wrinkles thereon.

EXAMPLE 3

Face firming cream:
  propylene glycol ... 1
  glycerylstearate PEG 100 ... 2
  sodium lauryl sulphate glycerylstearate ... 4
  glyceryl stearate ... 3
  cetylic alcohol ... 1
  caprilic/capric triglyceride ... 3
  octyl stearate ... 2
  avocado oil ... 1
  oil of camelia ... 1
  ascorbyl palmitate ... 0.5
  vitamin A palmitate ... 0.01
  wheat glycoceramides ... 0.1
  lactic acid ... 0.5
  Carbopol 940 ... 0.5
  magnesium ascorbyl phosphate ... 1
  water+preservative+perfumes ... qs for 100.

This cream is applied morning and night and gives back the elasticity to the face which then gives a good tone and a firm appearance.

EXAMPLE 4

Body care milk:
  vegetable oil ... 2
  caprylic/capric triglyceride ... 5
  vitamin E acetate ... 0.56
  carbomer ... 0.5
  xanthane gum ... 0.20
  hyaturonic acid ... 0.15
  sodium erythorbate ... 0.9
  ginseng extract ... 0.1
  Centella asiatica extract ... 0.1
  Green tea extract ... 0.05
  water+preservative+refreshing agent+perfume ... qs for 100.

In order to prevent any risk of degradation of oxidisable components, in particular sodium erythorbate, this composition is preferably manufactured and packaged without contact with oxygen, in particular without contact with air.

Application to the bust with massage in the evening in a treatment for 20 days in order to enable the tissues of the bust to retain their elasticity.

EXAMPLE 5

Firming lotion for the face

This lotion is obtained by extemporaneous mixture of 5 ml of lotion A with 100 mg of sodium L-ascorbate.

Lotion A
  madecassoside ... 1
  ginsenoside $R_o$ ... 1
  1% aqueous solution of hyaluronic acid ... 1
  glycerine ... 2
  water+preservative ... qs for 100.

This firming lotion may be marketed for example in the form of a small flask of 8 ml which contains the 100 mg of sodium L-ascorbate powder, and a sealed vial containing 5 ml of lotion A. At the moment of use, the contents of the vial are poured into the small flask and is agitated until the powder dissolves.

This extemporaneous preparation, which is used daily, improves the elasticity of the skin of the face and has therefore a firming effect.

The invention also covers all the equivalent techniques of the means described as well as their various combinations.

We claim:

1. A method of promoting elastin synthesis in dermis in vitro or in vivo comprising;
  administering an effective amount of a composition comprising, as the sole elastin synthesis promoting compound, a vitamin C compound selected from the group consisting of ascorbic acid, sodium ascorbate, magnesium ascorbate, sodium ascorbyl phosphate, magnesium ascorbyl phosphate, erythorbic acid, sodium erythorbate, ascorbyl acetate, ascorbyl propionate, ascorbyl palmitate, erythorbyl acetate, erythorbyl propionate and erythorbyl palmitate, or a combination thereof.

2. A method of cosmetic treatment for promoting elastin synthesis in dermis in vivo comprising;
  applying to the skin, an effective amount of a cosmetic composition comprising, as the sole elastin synthesis promoting compound, a vitamin C compound selected from the group consisting of ascorbic acid, sodium ascorbate, magnesium ascorbate, sodium ascorbyl phosphate, magnesium ascorbyl phosphate, erythorbic acid, sodium erythorbate, ascorbyl acetate, ascorbyl propionate, ascorbyl palmitate, erythorbyl acetate, erythorbyl propionate and erythorbyl palmitate, or a combination thereof and a cosmetically acceptable excipient.

3. A method of promoting elastin synthesis in cultured fibroblasts in vitro comprising;
  adding to a culture medium, an amount of an elastin synthesis promoting vitamin C compound selected from the group consisting of ascorbic acid, sodium ascorbate, magnesium ascorbate, sodium ascorbyl phosphate, magnesium ascorbyl phosphate, erythorbic acid, sodium erythorbate, ascorbyl acetate, ascorbyl propionate, ascorbyl palmitate, erythorbyl acetate, erythorbyl propionate and erythorbyl palmitate, or a combination thereof.

4. A method of treatment for promoting elastin synthesis in the dermis comprising;
  applying to the skin of a person in need thereof, an effective amount of a pharmaceutical composition comprising, as the sole elastin synthesis promoting compound, a vitamin C compound selected from the group consisting of ascorbic acid, sodium ascorbate, magnesium ascorbate, sodium ascorbyl phosphate, magnesium ascorbyl phosphate, erythorbic acid, sodium erythorbate, ascorbyl acetate, ascorbyl propionate, ascorbyl palmitate, erythorbyl acetate, erythorbyl propionate and erythorbyl palmitate, or a combination thereof and a pharmaceutically acceptable excipient.

5. The method according to claim 2 wherein the elastin synthesis promoting compound is present in the composition in an amount of from 0.001 to 5% by weight with respect to the total weight of the composition.

6. The method according to claim 2 wherein the elastin synthesis promoting compound is present in the composition in an amount of from 0.01 to 1% by weight with respect to the total weight of the composition.

7. The method according to claim 2 wherein the composition further comprises an active principle ingredient which promotes the synthesis of collagen.

8. The method of claim 7 wherein said active principle ingredient is selected from the group consisting of madecassoside, a Centrella asiatica extract and a ginseng extract or a combination thereof.

9. The method according to claim 2 wherein the composition further comprises an active principle ingredient which promotes the synthesis of a glycosaminoglycan.

10. The method according to claim 9 wherein said active principle ingredient is selected from the group consisting of a Filicium decipiens extract and platelet derived growth factor, or a combination thereof.

11. The method of claim 7 wherein the composition further comprises an active principle ingredient which promotes the synthesis of a glycosaminoglycan.

12. The method according to claim 2 wherein the composition further comprises a member selected from the group consisting of vitamin A, vitamin A palmitate, vitamin A proprionate, vitamin A acetate and vitamin E or a combination thereof at a concentration of from 0.0001 and 5% by weight with respect to the total weight of the composition.

13. The method according to claim 3 wherein the fibroblasts are human fibroblasts.

14. The method according to claim 3 wherein the elastin synthesis promoting compound is added at a concentration of from 5 and 150 micromoles per liter of culture medium.

15. The method according to claim 3 wherein the elastin synthesis promoting compound is added at a concentration of from 10 and 150 micromoles per liter of culture medium.

16. The method according to claim 4 wherein the elastin synthesis promoting compound is present in the composition in an amount of from 0.001 to 5% by weight with respect to the total weight of the composition.

17. The method according to claim 4 wherein the elastin synthesis promoting compound is present in the composition in an amount of from 0.01 to 1% by weight with respect to the total weight of the composition.

18. The method according to claim 4 wherein the composition further comprises an active principle ingredient which promotes the synthesis of collagen.

19. The method of claim 18 wherein said active principle ingredient is selected from the group consisting of madecassoside, a Centrella asiatica extract and a ginseng extract or a combination thereof.

20. The method according to claim 4 wherein the composition further comprises an active principle ingredient which promotes the synthesis of a glycosaminoglycan.

21. The method according to claim 20 wherein said active principle ingredient is selected from the group consisting of a Filicium decipiens extract and platelet derived growth factor, or a combination thereof.

22. The method of claim 18 wherein the composition further comprises an active principle ingredient which promotes the synthesis of a glycosaminoglycan.

23. The method according to claim 4 wherein the composition further comprises a member selected from the group consisting of vitamin A, vitamin A palmitate, vitamin A proprionate, vitamin A acetate and vitamin E or a combination thereof at a concentration of from 0.0001 and 5% by weight with respect to the total weight of the composition.

24. A method of cosmetic treatment for preventing or correcting a loss of skin elasticity, skin tone or skin firmness by promoting elastin synthesis in the dermis comprising;

applying to the skin, an effective amount of a cosmetic composition comprising, as the sole elastin synthesis promoting compound, a vitamin C compound selected from the group consisting of ascorbic acid, sodium ascorbate, magnesium ascorbate, sodium ascorbyl phosphate, magnesium ascorbyl phosphate, erythorbic acid, sodium erythorbate, ascorbyl acetate, ascorbyl propionate, ascorbyl palmitate, erythorbyl acetate, erythorbyl propionate and erythorbyl palmitate, or a combination thereof and a cosmetically acceptable excipient.

* * * * *